US00PP32728P3

(12) United States Plant Patent
Klemm et al.

(10) Patent No.: US PP32,728 P3
(45) Date of Patent: Jan. 5, 2021

(54) ***DAHLIA* PLANT NAMED 'KLEDH18119'**

(50) Latin Name: ***Dahlia* x *hybrida***
Varietal Denomination: KLEDH18119

(71) Applicant: Klemm+Sohn GmbH & Co. KG, Stuttgart (DE)

(72) Inventors: Nils Klemm, Stuttgart (DE); Maike Boxriker, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/602,795

(22) Filed: Dec. 3, 2019

(65) Prior Publication Data

US 2020/0196509 P1 Jun. 18, 2020

Related U.S. Application Data

(60) Provisional application No. 62/917,614, filed on Dec. 17, 2018.

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 5/02
See application file for complete search history.

(56) References Cited

PUBLICATIONS http://www.who-sells-it.com/cy/ball-seed-6773/2019-selecta-63299/page-116.html; Oct. 26, 2019; 1 page.*

* cited by examiner

*Primary Examiner* — Kent L Bell
(74) *Attorney, Agent, or Firm* — Weatherly IP Solutions, LLC; Barbara Campbell

(57) ABSTRACT

A new *Dahlia* plant designated 'KLEDH18119' particularly distinguished by red inflorescences and a compact and semi-upright plant habit, is disclosed.

1 Drawing Sheet

Genus and species: *Dahlia* x *hybrida*.
Variety denomination: 'KLEDH18119'.

BACKGROUND

The present invention comprises a new and distinct variety of *Dahlia*, botanically known as *Dahlia* x *hybrida*, and hereinafter referred to by the variety name 'KLEDH18119'. 'KLEDH18119' originated from an open pollination of the female *Dahlia* parent 'DH-2014-1288' (unpatented) in Stuttgart, Germany in 2014.

In 2015 a seedling was selected and named 'KLEDH18119'. In 2016, 'KLEDH18119' was first vegetatively propagated by vegetative stem cuttings. 'KLEDH18119' was found to reproduce true to type in successive generations of asexual propagation in Stuttgart, Germany and Latina, Italy via vegetative stem cuttings.

SUMMARY

The following are the most outstanding and distinguishing characteristics of 'KLEDH18119' when grown under normal horticultural practices in Stuttgart, Germany.

1. Red inflorescences; and
2. A compact, semi-upright habit.

DESCRIPTION OF THE PHOTOGRAPH

This new *Dahlia* plant is illustrated by the accompanying photograph of a plant of 'KLEDH18119' approximately 11 to 12 weeks old and grown in a greenhouse in Stuttgart, Germany. The photograph is of a whole plant, including the inflorescences and foliage and buds and was taken in May 2018 in Stuttgart, Germany. The colors shown are as true as can be reasonably obtained by conventional photographic procedures.

DESCRIPTION

The following detailed descriptions set forth the distinctive characteristics of 'KLEDH18119'. The data which define these characteristics were collected from asexual reproductions carried out in Stuttgart, Germany. Data was collected on plants potted the week of Jun. 11, 2018 and grown in a plastic greenhouse. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* x *hybrida*.
- *Designation*.—'KLEDH18119'.

Parentage:
- *Female parent*.—'DH-2014-1288' (unpatented).
- *Male parent*.—Unknown.

Plant:
- *Plant and growth habit*.—Compact, semi-upright, free basal branching, and inflorescences held above the foliar plane.
- *Plant height*.—37.0 cm.
- *Plant diameter or spread*.—43.0 cm.
- *Propagation type*.—Vegetative stem cuttings.
- *Time to produce a rooted young plant*.—8 to 9 weeks.

*Rooting habit*.—Freely branching and moderately dense.
*Root description*.—Fine and white.

Lateral branches:
*Length*.—25.0 cm.
*Diameter*.—0.7 cm.
*Internode length*.—3.0 cm.
*Aspect*.—Outwardly spreading.
*Strength*.—Strong.
*Texture*.—Smooth.
*Color*.—RHS 148A.

Foliage:
*Arrangement*.—Opposite, pinnately compound.
*Length*.—8.0 cm.
*Width*.—3.9 cm.
*Shape*.—Pinnate.
*Apex*.—Acute.
*Base*.—Acute.
*Margin*.—Lobed.
*Venation pattern*.—Pinnate.
*Venation color*.—Upper surface: RHS 178B. Lower surface: RHS 177A.
*Texture* (*both upper and lower surfaces*).—Smooth.
*Immature leaf color*.—Upper surface: RHS N137A. Lower surface: RHS 148C.
*Mature leaf color*.—Upper surface: RHS N189A. Lower surface: RHS 148B.

Petioles:
*Length*.—1.5 cm.
*Diameter*.—0.5 cm.
*Texture* (*both surfaces*).—Smooth.
*Color*.—Upper surface: RHS 144C and RHS N77A. Lower surface: RHS 144C and RHS N77A.

Inflorescence:
*Appearance and arrangement*.—Daisy-eyed double inflorescences held above the foliage.
*Fragrance*.—Present.
*Time to flower*.—In the winter about 3 months after planting; in the summer, about 2 months after planting.
*Post-production longevity*.—Plants flower continuously from spring through autumn; lastingness of the bloom is 150 days.
*Diameter*.—6.0 cm.
*Depth*.—4.0 cm.
*Disc diameter*.—1.5 cm.
*Receptacle height*.—0.5 cm.
*Receptacle diameter*.—1.5 cm.
*Receptacle color*.—RHS 143A.

Inflorescence bud:
*Height*.—0.5 cm.
*Diameter*.—1.0 cm.
*Shape*.—Circular.
*Color*.—RHS 137A.

Ray florets:
*Quantity per inflorescence*.—50 in about 3 to 4 whorls.
*Length*.—2.5 cm.
*Width*.—2.0 cm.
*Shape*.—Ovate.
*Apex*.—Rounded.
*Base*.—Rounded.
*Margin*.—Entire.
*Aspect*.—Semi-upright.
*Texture* (*both surfaces*).—Smooth.
*Color, immature, both surfaces*.—RHS 45A.
*Color, mature, both surfaces*.—RHS 45A.

Disc florets:
*Quantity per inflorescence*.—About 60.
*Length*.—1.0 cm.
*Diameter*.—0.2 cm.
*Shape*.—Tubular.
*Texture* (*both inner and outer surfaces*).—Smooth.
*Color*.—Immature (both inner and outer surfaces): RHS 46A. Mature (both inner and outer surfaces): RHS 53A.

Phyllaries:
*Quantity per inflorescence*.—10.
*Length*.—1.5 cm.
*Width*.—0.7 cm.
*Shape*.—Elliptic.
*Apex*.—Acute.
*Base*.—Acute.
*Margin*.—Entire.
*Texture* (*both surfaces*).—Smooth.
*Color* (*both surfaces*).—RHS 146A.

Peduncles:
*Length, terminal peduncle*.—Up to 15.0 cm.
*Length, axillary peduncle*.—5.0 cm to 15.0 cm.
*Diameter*.—0.4 cm.
*Aspect*.—Semi-upright.
*Strength*.—Strong.
*Texture*.—Smooth.
*Color*.—RHS N199A.

Reproductive organs:
*Androecium*.—Present on ray florets. Quantity per floret: 2. Filament length: 0.7 cm. Filament color: RHS 1B. Anther shape: Long lanceolate. Anther length: 0.3 cm. Anther color: RHS 13A. Pollen amount: Sparse. Pollen color: RHS 9A.
*Gynoecium*.—Present on both ray florets and disc florets. Quantity per floret: 1. Pistil length: 1.0 cm. Style length: 0.5 cm. Style color: RHS 14A. Stigma shape: Lanceolate pinnate. Stigma color: RHS 1B. Ovary color: RHS 1C.

Fruit and seed set: No fruit or seed set observed.

Disease and pest/insect resistance: Moderate Mildew resistance is observed.

COMPARISON OF 'KLEDH18119' WITH PARENTAL LINE AND KNOWN VARIETY

'KLEDH18119' is distinguished from the female parent as described in Table 1.

TABLE 1

Comparison with Parental Line

| Characteristic | 'KLEDH18119' | Female Parent 'DH-2014-1288' |
|---|---|---|
| Ray floret color | Red | Purple |

'KLEDH18119' can be compared to the commercial *Dahlia* variety 'Mariana' (Unpatented). Differences between the varieties are described in Table 2.

TABLE 2

Comparison with Similar Variety

| Characteristic | 'KLEDH18119' | 'Mariana' |
|---|---|---|
| Mildew resistance | Moderate | Susceptible |
| Foliage | Dark green | Green |

We claim:

1. A new and distinct variety of *Dahlia* plant designated 'KLEDH18119' as illustrated and described herein.

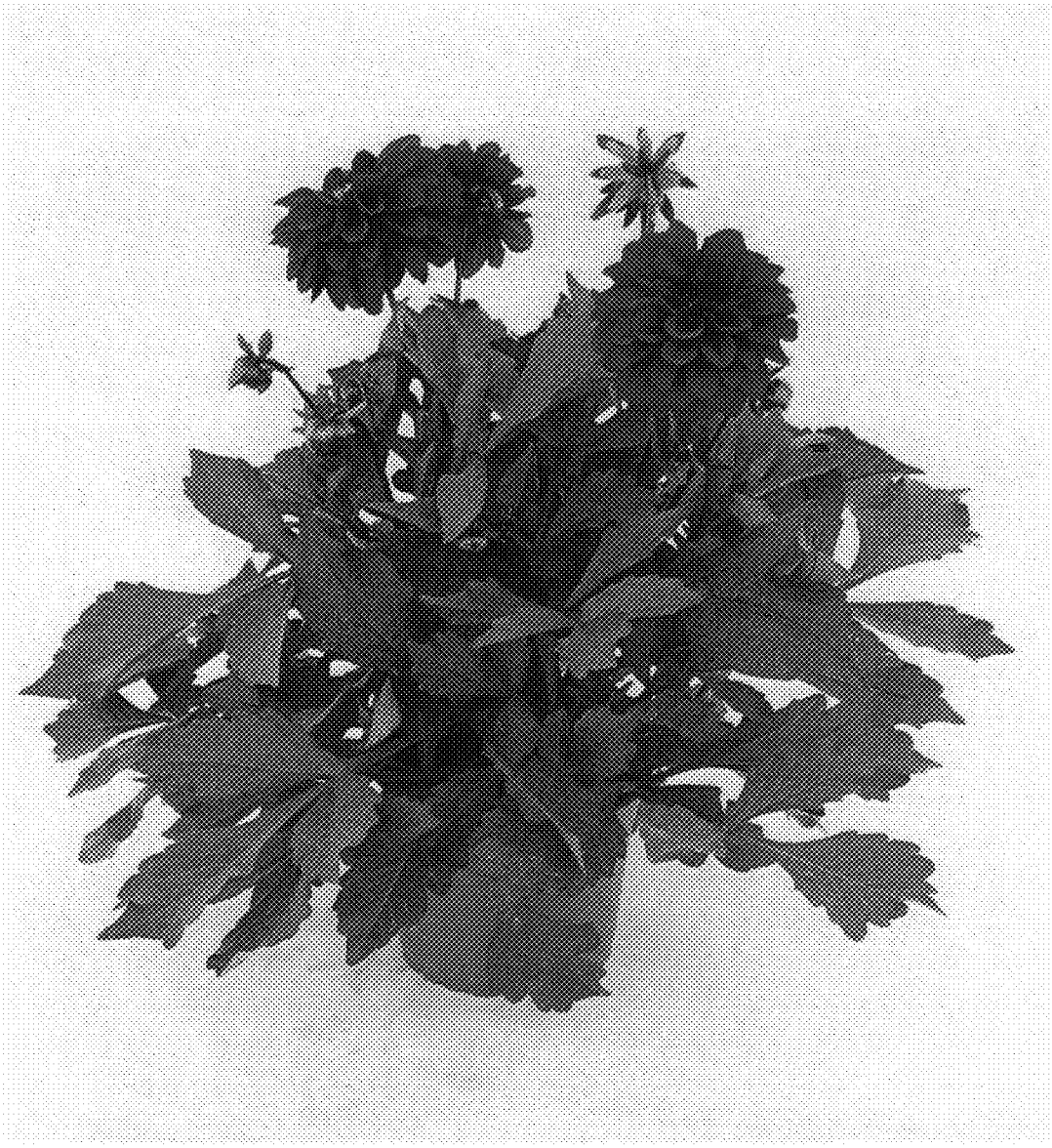

* * * * *